United States Patent
Nakamura et al.

[11] Patent Number: 5,645,520
[45] Date of Patent: Jul. 8, 1997

[54] SHAPE MEMORY ALLOY ACTUATED ROD FOR ENDOSCOPIC INSTRUMENTS

[75] Inventors: Yoshihiko Nakamura, Tokyo; Minoru Hashimoto, Kagoshima, both of Japan

[73] Assignee: Computer Motion, Inc., Goleta, Calif.

[21] Appl. No.: 322,778

[22] Filed: Oct. 12, 1994

[51] Int. Cl.$^6$ ........................................... A61B 1/00
[52] U.S. Cl. .................... 600/151; 600/153; 600/143; 604/281; 606/78
[58] Field of Search ............................. 600/151, 143, 600/152; 604/281; 606/78, 192; 901/2, 14, 27

[56] References Cited

U.S. PATENT DOCUMENTS

| | | | |
|---|---|---|---|
| 4,815,450 | 3/1989 | Patel | 600/151 X |
| 4,954,952 | 9/1990 | Ubhayakar et al. | 364/513 |
| 4,969,709 | 11/1990 | Sogawa et al. | 600/151 X |
| 4,969,890 | 11/1990 | Sugita et al. | 606/192 |
| 5,097,829 | 3/1992 | Quisenberry | 128/400 |
| 5,309,717 | 5/1994 | Minch | 60/527 |

*Primary Examiner*—Richard J. Apley
*Assistant Examiner*—Beverly M. Flanagan
*Attorney, Agent, or Firm*—Kenneth L. Stein

[57] ABSTRACT

A construction element that contains a shape memory element which changes shape in response to a change in the temperature of the memory element. The temperature is varied by a fluid which flows through channels adjacent to the shape memory element. The fluid typically flows through an inner channel of the memory element and an outer element formed by the element and an outer elastic pipe. A plurality of shape memory elements can be coupled together to create a robotic arm or an endoscopic instrument. The arm or endoscope can change shape by varying the temperature of the fluid. The fluid temperature and the corresponding shape of the arm/endoscope can be controlled by a computer.

5 Claims, 2 Drawing Sheets

SHAPE MEMORY ALLOY ACTUATED ROD FOR ENDOSCOPIC INSTRUMENTS

BACKGROUND OF THE INVENTION

1. Field of the Invention

The present invention relates to an endoscopic instrument that is constructed from a shape memory alloy which varies shape in response to a change in temperature.

2. Description of Related Art

Non-invasive surgical procedures are typically performed with a laparoscope that is inserted through a small incision in the patient. Conventional laparoscopes contain a tube which has an inner channel. The inner channel may contain fiber optic cable that is coupled to a lens located at the end of the laparoscope. The fiber optic cable is coupled a camera and a monitor which displays the organs of the patient.

The laparoscopic tube is relatively stiff and is typically moved in a linear manner. The linear movement of the laparoscope may be impeded by an organ or another structure. It would be desirable to provide a laparoscope that can bend within a patient to improve the maneuverability of the instrument.

Laparoscopes are typically held by the surgeon or a surgical assistant during a procedure. Having to continually hold the instrument may result in fatigue. Additionally, if held by an assistant, the laparoscope is moved in response to instructions from the surgeon. The instructions may be misunderstood by the assistant, or miscommunicated by the surgeon, thereby resulting in an error in the manipulation of the instrument. It would therefore be desirable to provide a laparoscope that automatically moves within a patient in response to a command by the surgeon.

SUMMARY OF THE INVENTION

The present invention is a construction element that contains a shape memory element which changes shape in response to a change in the temperature of the memory element. The temperature is varied by a fluid which flows through channels adjacent to the shape memory element. The fluid typically flows through an inner channel of the memory element and an outer element formed by the element and an outer elastic pipe. A plurality of shape memory elements can be coupled together to create a robotic arm or an endoscopic instrument. The arm or endoscope can change shape by varying the temperature of the fluid. The fluid temperature and the corresponding shape of the arm/endoscope can be controlled by a computer.

BRIEF DESCRIPTION OF THE DRAWINGS

The objects and advantages of the present invention will become more readily apparent to those ordinarily skilled in the art after reviewing the following detailed description and accompanying drawings, wherein.

DETAILED DESCRIPTION OF THE INVENTION

Figure 1:
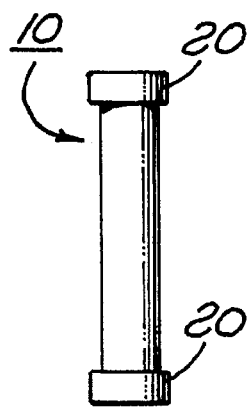
FIG. 1 is a side view of a construction element of the present invention.
Figure 2:
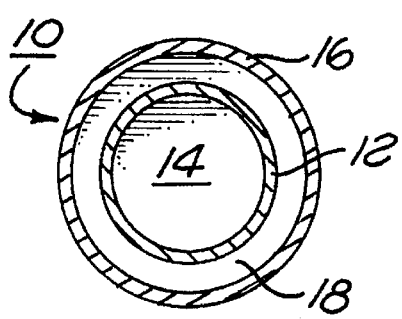
FIG. 2 is a cross-sectional view of the construction element.

Referring to the drawings more particularly by reference numbers, FIGS. 1 and 2 show a construction element 10 of the present invention. The construction element 10 contains a shape memory element 12 that changes shape when the temperature of the element is varied. The memory element 12 is typically relatively flexible and non-elastic when below a threshold temperature T1, and is relatively stiff, elastic and has a predefined shape when above a threshold temperature T2. The element will have intermediate stillnesses and shapes between the threshold temperatures T1 and T2. The shape memory element 12 may be constructed from a metal alloy such as a titanium-nickel material sold by Tokin Corp., or any other type of material that will change shape as a function of temperature.

The shape memory element 12 may be constructed as a tube which has an inner channel 14. In the preferred embodiment, the shape memory element 12 is located within an elastic pipe 16. The memory element 12 may be separated from the elastic pipe 16 by a second channel 18. The channels 14 and 18 may be enclosed by caps 20 located at the ends of the memory element 12 and pipe 16. One of the caps 20 may have openings (not shown) that allow a fluid to flow through the channels 14 and 18. By way of example, the fluid may flow through the outer channel 18 and back through the inner channel 14. The return path from the outer channel 18 to the inner channel 14 may be at the end of the element opposite from the cap openings, through holes in the memory element 12 along the length of the element, or any other means to create a flow of fluid through the construction element 10.

Figure 3:
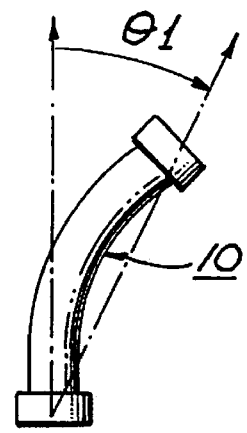
FIG. 3 is a side view similar to FIG. 1 showing the shape of the element in an intermediate position.
Figure 4:
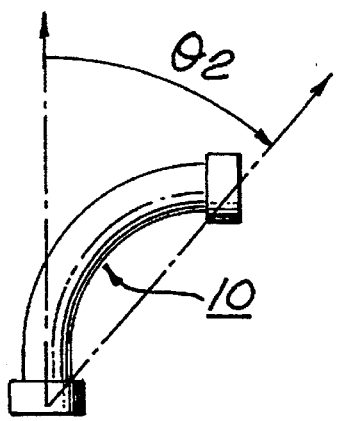
FIG. 4 is a side view similar to FIG. 3, showing the shape of the element in a fully bent position.

The temperature of the fluid is varied to change the shape of the memory element. As shown in FIG. 3, when the temperature of the fluid is varied to a value between T1 and T2 the memory element 12 changes shape and bends the construction element 10 an angle θ1. As shown in FIG. 4, when the fluid temperature is above T2 the element bends to a second angle θ2. The angle θ is a function of the shape of the memory element at the specified temperature and the stiffness of the outer elastic pipe 14. A relatively rigid outer pipe 14 will reduce the bend angle θ of the construction element 10.

Figure 5:
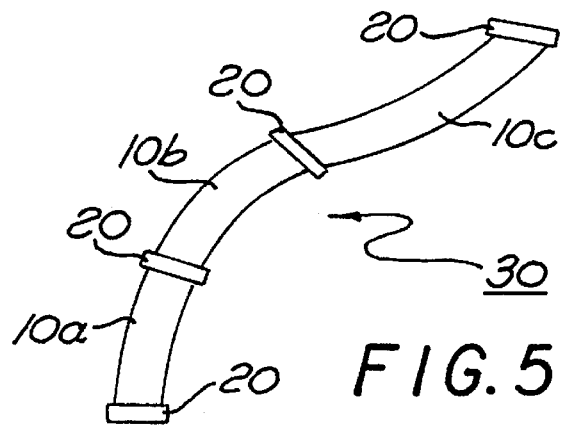
FIG. 5 is a side view showing a plurality of construction elements that are combined to form a robotic arm.

As shown in FIG. 5, a plurality of construction elements 10 can be combined to create a manipulator arm 30 which has multiple degrees of freedom. Both caps of the intermediate element 10b can have openings to allow fluid communication between all of the elements 10a, 10b and 10c so that the temperature of each element can be varied by the fluid. Each construction element 10 may have a predefined shape (eg. shape of element when at or above temperature T2) that is different than the predefined shape of the other construction elements. The multiple shape elements 10 provide an arm which can bend in different directions and at various angles. For example, the construction element 10a can be constructed to have a predefined shape angle θ2 that is less than the predefined shape angle µ2 of construction element 10b. Furthermore, construction element 10c can bend in a direction opposite from the bend direction of elements 10a and 10b. The different shapes can be accomplished by creating specific individual shapes for each memory element and/or elastic pipe. For example, a construction element 10 may be given a smaller bend angle θ, by creating a memory element 12 with a predefined shape at T2 that is relatively small, or by providing a more rigid outer pipe 14, or by providing an outer pipe 14 that has a pre-existing bend in a direction opposite from the bend direction of the memory element 12, and so forth and so on.

Figure 6:
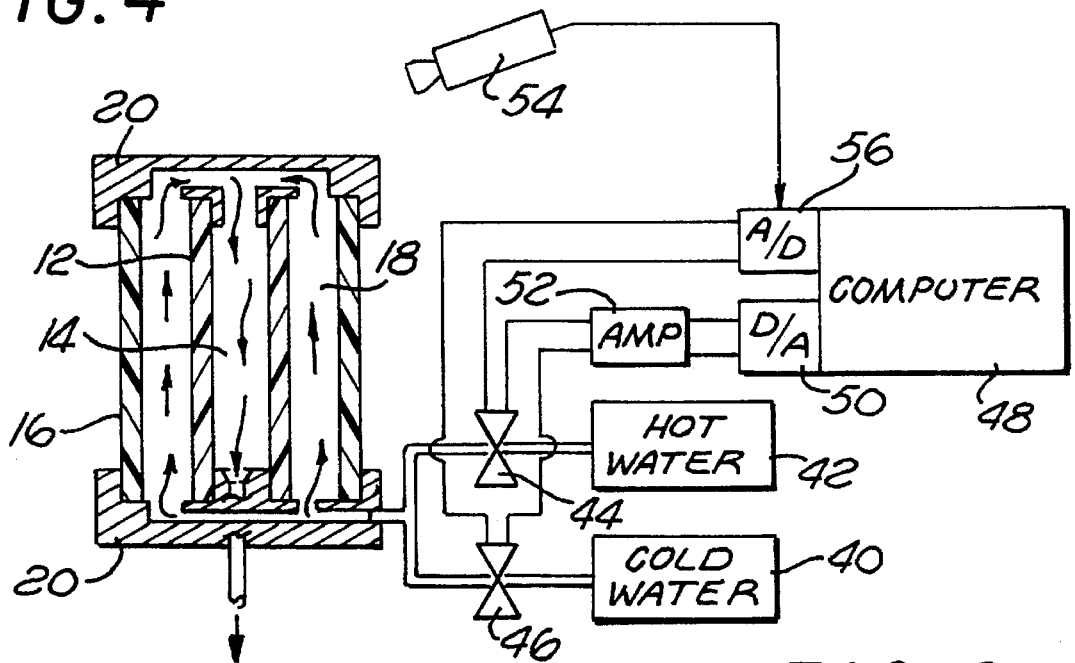
FIG. 6 is a schematic of a construction element coupled to a computer controlled fluid system.

FIG. 6 shows a system for controlling the shape of a construction element 10. The system has a cold fluid tank 40 and a hot fluid tank 42 that are coupled to the outer channel 18 of the construction element 10. The inner channel 14 of the element 10 can be connected to a drain or looped back to the fluid tanks. The fluid can be any substance such as water, oil, gas, etc. that transfers heat to or from the memory element 12.

The flow of fluid from the hot tank 40 is controlled by a hot valve 44. Likewise, the flow of fluid from the cold tank 42 is controlled by a cold valve 46. The valves 44 and 46 typically contain a solenoid that is actuated by a computer 48. The valve actuation signal is typically converted from a computer generated digital command to an analog signal by an digital to analog (D/A) converter 50. The analog signal may be amplified by amplifier 52. As an alternate embodiment, the valves 44 and 46 may be pumps that are energized and deenergized by the computer. If valves are employed, the tanks should be pressurized to induce a flow of fluid.

The computer 48 generates commands to control the temperature of the fluid and the shape of the construction element 10. For example, the computer 48 may bend the construction element by generating a command that opens the hot valve 44 and maintains the cold valve 46 in a closed position. Opening the hot valve 44 allows hot fluid to flow through the construction element 10 and raise the memory element 12 above the threshold temperature T2, so that the element bends to the angle θ2. Likewise, the construction element 10 can be returned to the original position by opening the cold valve 46 and closing the hot valve 44. Intermediate element positions can be obtained by opening both valves 44 and 46 to create a desired fluid temperature.

The system may have a feedback system 54 that senses the actual position of the construction element 10. The feedback system 54 may be optical, electrical or mechanical in nature and typically provides an analog feedback signal(s) that is converted to a digital format by an analog to digital (A/D) converter 56. If the feedback systems senses that the construction element 10 is not at a desired position, the computer 48 can vary the fluid temperature, accordingly. The fluid control system may also have fluid flow and/or fluid temperature feedback signals that are provided to the computer 48 through the A/D converter 50. For devices that have multiple construction elements the system may have a plurality of valves 44 and 46, wherein each pair of valves 44 and 46 are dedicated to a specific element so that the computer 48 can control the fluid temperature and corresponding shape of each construction element on an individual basis.

Figure 7:
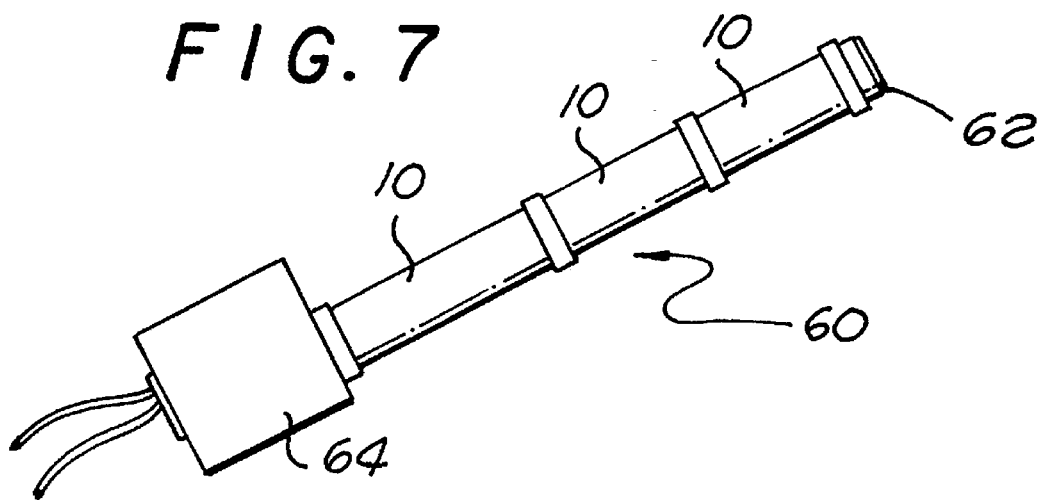
FIG. 7 is a perspective of a laparoscope constructed from a plurality of construction elements.
Figure 8:
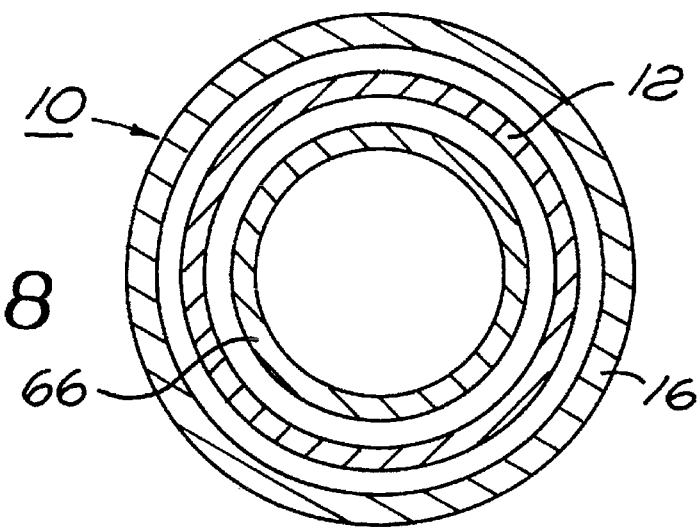
FIG. 8 is a cross-sectional view of the laparoscope of FIG. 7.

FIG. 7 shows a laparoscope 60 constructed from a plurality of construction elements 10. The laparoscope 60 may have a lens 62 located at one end and a camera 64 located at the opposite end of the scope. The lens 62 is typically connected to the camera by a fiber optic cable (not shown). As shown in FIG. 8, the laparoscope 60 may have an additional inner elastic pipe 66 that provides a conduit for fiber optic cable, electrical wires, etc. The inner elastic pipe 66 also further defines the shape of the overall construction element. The shape of the laparoscope can be controlled by the system shown in FIG. 6. The computer may have a manual input device (not shown) such as a foot pedal or a hand controller, or a speech interface that allows a surgeon to provide inputs that control the shape of the laparoscope. For example, the surgeon may provide an input command to bend the lens 62 to the left. The computer 48 can interpret the command and vary the fluid temperature so that the laparoscope 60 bends to the left. The changing shape of the laparoscope allows the surgeon to view the internal organs of the patient in response to commands from the surgeon. Although the element 10 shown in FIG. 8 is referred to as a laparoscope, it is to be understood that the combination of an inner pipe 66, memory element 12 and outer pipe 14 can be used for other endoscopic instruments. For example, the surgical instrument may have a medical end effector mounted at one end of the instrument, and wire, cables, etc. that extend through the inner pipe 66.

Figure 9:
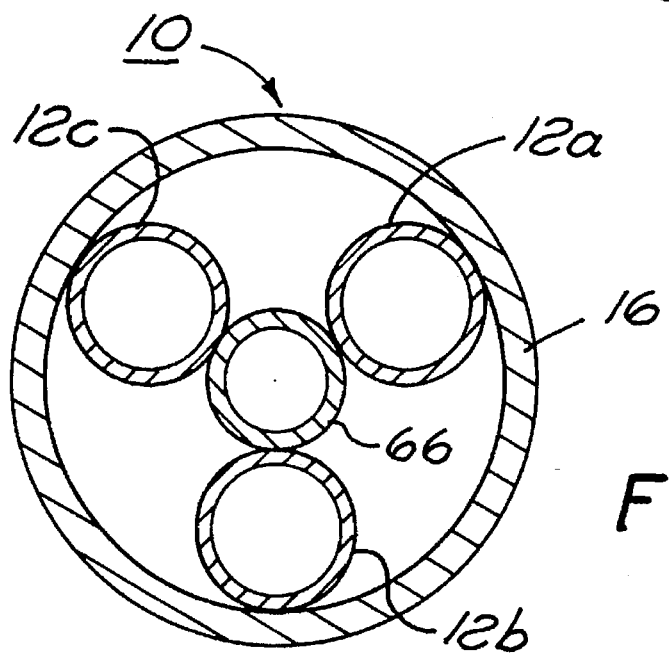
FIG. 9 is a cross-sectional view of an alternate embodiment of the laparoscope.

FIG. 9 shows an alternate embodiment of a construction element which has a plurality of memory elements 12 located within the same outer elastic pipe 16. The pre-taught shapes of each memory element can be varied to provide construction elements that bend into a variety of angles and directions. For example, memory element 12a may bend in a direction opposite from the bend directions of elements 12b and 12c. Additionally, the memory elements can be coupled to separate fluid control valves so that the memory elements 12a, 12b and 12c each have a different temperature control, thereby providing a range of construction element shapes and positions. The construction element may have an inner elastic pipe 66 that provides a conduit for fiber optic cable, electrical wires, etc.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A surgical instrument comprising a bendable mechanical arm, wherein the arm comprises:

a first tube;

a second tube, the second tube formed of a shape memory alloy and having a diameter smaller than the first tube, the second tube nested within the first tube thus defining a gap between the first tube and the second tube, the gap configured to provide a passageway for fluid to flow therethrough such that the second tube deflects at an angle in response to the temperature of the fluid flowing through the gap;

means for providing fluid flow through the gap;

means for controlling the temperature of the fluid provided by the means for providing fluid flow; and wherein the means for providing fluid flow and the means for controlling the temperature are in electrical communication.

2. The arm of claim 1 wherein the means for controlling the temperature comprises a programmed computer.

3. The arm of claim 2 wherein the means for controlling the temperature of the fluid further comprises at least one computer operated valve.

4. The arm of claim 3 wherein the means for controlling the temperature of the fluid further comprises an analog to digital converter.

5. The arm of claim 4 wherein the means for controlling the temperature of the fluid further comprises a digital to analog converter.

* * * * *